DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 1, 1971

827 O.G. 5

T887,006

KETOVINYL COMPOUNDS AND PHOTOGRAPHIC HARDENERS

Donald M. Burness and Robert A. Silverman, both of Kodak Park Works, Rochester, N.Y. 14650

Filed Apr. 23, 1970, Ser. No. 31,350
Int. Cl. C07c *53/16;* G03c *1/30*
U.S. Cl. 96—111
No Drawing. 21 Pages Specification

Compounds having the structure:

$$RCH{=}CHCO(ZCO)_mCH{=}CHR$$

wherein Z is a covalent bond or a divalent hydrocarbon radical such as an alkylene radical, a cycloalkylene radical or an arylene radical; $m=0$ to 1 and R is selected from alkoxy, halo, arylthio, secondary and tertiary amino groups and $-B^+X^-$ wherein $B^+$ is selected from an ammonium salt residue such as trialkylammonium, dialkylhydrazinium or a heterocyclic ammonium salt residue having 5–6 atoms in the heterocyclic ring, either unsubstituted or substituted and $X^-$ is an acid anion, such as chloride, bromide, fluoride, iodide, perchlorate, methanesulfonate, benzenesulfonate, toluenesulfonate or fluoroborate, have been found to exhibit strong activity as gelatin hardeners. Compositions comprising gelatin and the hardener compounds and gelatin-silver halide photographic emulsions containing the hardener compounds are disclosed. 3,8-dioxo-1,9-decadiene-1,10-bis(pyridinium chloride); 1,10-dichloro-1,9-decadiene-3,8-dione; 1,10-dipiperidino-1,9-decadiene-3,8-dione; 3,8-dioxo-1,9-decadiene-1,10-bis(trimethylammonium perchlorate) and 3-oxo-1,4-pentadiene-1,5-bis(pyridinium chloride) are representative hardener compounds.